United States Patent
Marmor et al.

(10) Patent No.: US 10,492,699 B2
(45) Date of Patent: Dec. 3, 2019

(54) DETERMINATION OF VENTRICULAR PRESSURE AND RELATED VALUES

(71) Applicant: CORALERT LTD., Ramat Hasharon (IL)

(72) Inventors: Alon Marmor, Kfar Hanania (IL); Amir Marmor, Arugot (IL)

(73) Assignee: CORALERT LTD., Ramat Hasharon (IL)

( * ) Notice: Subject to any disclaimer, the term of this patent is extended or adjusted under 35 U.S.C. 154(b) by 590 days.

(21) Appl. No.: 14/435,212

(22) PCT Filed: Oct. 8, 2013

(86) PCT No.: PCT/IL2013/050815
§ 371 (c)(1),
(2) Date: Apr. 13, 2015

(87) PCT Pub. No.: WO2014/057489
PCT Pub. Date: Apr. 17, 2014

(65) Prior Publication Data
US 2015/0265163 A1    Sep. 24, 2015

Related U.S. Application Data

(63) Continuation of application No. 13/649,857, filed on Oct. 11, 2012, now abandoned.

(51) Int. Cl.
*A61B 5/02*     (2006.01)
*A61B 5/0225*   (2006.01)
(Continued)

(52) U.S. Cl.
CPC ........... *A61B 5/0225* (2013.01); *A61B 5/026* (2013.01); *A61B 5/02007* (2013.01);
(Continued)

(58) Field of Classification Search
CPC .............. A61B 5/02028; A61B 5/72; A61B 2562/0204
See application file for complete search history.

(56) References Cited

U.S. PATENT DOCUMENTS 4,203,451 A * 5/1980 Panico ............... A61B 5/022
600/485
5,199,438 A * 4/1993 Pearlman ........... A61B 5/02028
600/483
(Continued)

FOREIGN PATENT DOCUMENTS

| WO | WO8303970 | 11/1983 |
| WO | 2005046467 | 5/2005 |
| WO | WO-2007/091244 | 8/2007 |

OTHER PUBLICATIONS

European Partial Search of EP Application No. 13845110.9 dated Jul. 22, 2016.
(Continued)

*Primary Examiner* — Puya Agahi
(74) *Attorney, Agent, or Firm* — The Roy Gross Law Firm, LLC; Roy Gross

(57) ABSTRACT

A method and a device for determining a cardiac function parameter, the device including a sonic sensor for determining timing data of a closure of a mitral valve and an aortic valve, a pressure cuff and a sensing unit coupled to the pressure cuff for sensing. The sensing unit is configured to sense, for each cardiac cycle, blood breakthrough pressure data and corresponding time data from a closing of the mitral valve and data relating to a velocity of propagation of a pressure wave as it travels along at least a portion of the pressure cuff. The device also includes a processing unit for determining a value of at least one cardiac function parameter based on the data.

20 Claims, 11 Drawing Sheets

(51) Int. Cl.

| | | |
|---|---|---|
| *A61B 5/00* | (2006.01) | |
| *A61B 7/00* | (2006.01) | |
| *A61B 5/021* | (2006.01) | |
| *A61B 5/026* | (2006.01) | |
| *A61B 5/0215* | (2006.01) | |
| *A61B 7/04* | (2006.01) | |
| *A61M 5/172* | (2006.01) | |
| *A61B 5/022* | (2006.01) | |

(52) U.S. Cl.
CPC ........ *A61B 5/0215* (2013.01); *A61B 5/02028* (2013.01); *A61B 5/02125* (2013.01); *A61B 5/6876* (2013.01); *A61B 5/72* (2013.01); *A61B 5/7278* (2013.01); *A61B 7/00* (2013.01); *A61B 7/045* (2013.01); *A61M 5/1723* (2013.01); *A61B 5/022* (2013.01); *A61B 5/4839* (2013.01); *A61B 5/7225* (2013.01); *A61B 5/7246* (2013.01); *A61B 2562/0204* (2013.01); *A61B 2562/0247* (2013.01)

(56) References Cited

U.S. PATENT DOCUMENTS

| | | | |
|---|---|---|---|
| 6,010,457 | A | 1/2000 | O'Rourke |
| 6,334,849 | B1 | 1/2002 | Sunagawa |
| 6,355,000 | B1 | 3/2002 | Ogura |
| 7,139,609 | B1 | 11/2006 | Min et al. |
| 2003/0144572 | A1 | 7/2003 | Oschman et al. |
| 2003/0153837 | A1 | 8/2003 | McIntyre |
| 2003/0153839 | A1 | 8/2003 | Nomura |
| 2003/0204145 | A1 | 10/2003 | Manolas |
| 2004/0172079 | A1 | 9/2004 | Chinchoy |
| 2004/0186524 | A1 | 9/2004 | Chinchoy |
| 2005/0154370 | A1 | 7/2005 | Sigg et al. |
| 2008/0161566 | A1 | 7/2008 | Unver et al. |
| 2008/0294019 | A1* | 11/2008 | Tran ............... A61B 5/0006 600/301 |
| 2009/0030328 | A1 | 1/2009 | Harpas et al. |
| 2009/0030471 | A1* | 1/2009 | Rousso ............ A61N 1/3627 607/27 |
| 2009/0287097 | A1 | 11/2009 | Lowe |
| 2011/0160790 | A1 | 6/2011 | Stegemann et al. |

OTHER PUBLICATIONS

Office Action issued for U.S. Appl. No. 13/649,857 dated Jun. 5, 2015.

Marmor, A. et al.; "Method for Noninvasive Measurement of Central Aortic Systolic Pressure", Clin. Cardiol. 10, 1987, pp. 215-221.

Sharir, T. et al.; "Validation of a Method for Noninvasive Measurement of Central Arterial Pressure", Hypertension vol. 21, No. 1, Jan. 1993, pp. 74-82.

Camacho Fernando, Thesis "Statistical Analysis of Central Aortic Pressure Parameters Derived From the Peripheral Pulse", Jan. 1, 2005, pp. 3, 18, 48-63.

J. R. Womersley, "Method for the Calculation of Velocity, Rate of Flow and Viscous Drag in Arteries When the Pressure Gradient is Known", J. Physiol, Jan. 1, 1955, pp. 553-563.

International Search Report for International Application No. PCT/IL2013/050815 dated Mar. 4, 2014.

* cited by examiner

Ischemia determining device
810

Sensor
820

Output
830

DETERMINATION OF VENTRICULAR PRESSURE AND RELATED VALUES

CROSS-REFERENCE TO RELATED APPLICATIONS

This application is a National Phase of International Application No. PCT/IL2013/050815, filed Oct. 8, 2013, claiming priority from U.S. patent application Ser. No. 13/649,857, filed Oct. 11, 2012, which is hereby incorporated by reference.

FIELD OF THE INVENTION

The present invention relates to non invasive determination of diagnostic values related to the heart. In particular the present invention relates to the determination of ventricular pressure and related values.

BACKGROUND OF THE INVENTION

During the systole portion of the cardiac cycle ventricular pressure may be equal to the aortic pressure immediately prior to the opening of the aortic valve and the pumping of blood into the body from the heart. A measurement of an elevated left ventricular pressure above an average reading has diagnostic value for the health of a patient.

Left ventricular pressure and aortic pressure may be determined accurately via invasive procedures. In addition, other diagnostic values such as the left ventricular end-diastolic pressure, e.g., the pressure of blood entering the heart from the lungs may also be of value as a diagnostic tool, and may also be determined via invasive procedures, for example, via pulmonary artery catheterization through the femoral vein in the leg where the catheter may be advanced toward the heart to determine the pressure values. A non-invasive determination of left ventricular pressure may have numerous clinical applications.

SUMMARY OF THE INVENTION

There is thus provided in accordance with some embodiments of the present invention, a device for determining a cardiac function parameter, the device including There is thus provided in accordance with some embodiments of the present invention, a device for determining a cardiac function parameter, the device including a sonic sensor for determining timing data of the closure of the mitral and aortic valves, a pressure cuff, a sensing unit coupled to the pressure cuff for sensing. The sensing unit coupled to the pressure cuff for sensing for each cardiac cycle, blood breakthrough pressure data and corresponding time data from the closing of the mitral valve, data relating to a velocity of propagation of a pressure wave as it travels along at least a portion of the pressure cuff; and, a processing unit for determining a value of at least one cardiac function parameter based on the data.

Furthermore, in accordance with some embodiments of the present invention, said at least one cardiac function parameter is selected from the group of cardiac function parameters consisting of end diastolic pressure, max dP/dT, isovolumetric contraction time, systemic vascular resistance, and central aortic pressure.

Furthermore, in accordance with some embodiments of the present invention, the sonic sensor is a microphone.

Furthermore, in accordance with some embodiments of the present invention, the sensing unit comprises at least two sensors.

Furthermore, in accordance with some embodiments of the present invention, said at least two sensors are selected from the group of sensors consisting of pressure sensors and Doppler sensors.

Furthermore, in accordance with some embodiments of the present invention, said at least one cardiac function parameter is max dP/dT, and wherein the processing unit is configured to iteratively calculate cardiac pressure and related values by calculating the slope of the tangent to a pressure waveform at a time point where the aortic valve opens.

Furthermore, in accordance with some embodiments of the present invention, said at least one cardiac function parameter is max dP/dT, and wherein the processing unit is configured to calculate an integral of a second derivative of a polynomial function.

Furthermore, in accordance with some embodiments of the present invention, said at least one cardiac function parameter is an end diastolic pressure, and wherein the processing unit is configured to calculate the end diastolic pressure using the equation:

$$pov = \left(\frac{1}{2} \times \frac{\max \frac{dP}{dT}}{\omega}\right) \times (1 - \cos(\omega t)) + EDP$$

where:
pmax is the pressure that a isovolumetrically contracting left ventricle would produce from the end diastolic volume if ejection of blood from the ventricle would be prevented; max dP/dT is the maximum isovolumetric pressure rate in the left ventricle; $\omega$ is the angular frequency; EDP is an end diastolic pressure value; pov is the pressure at opening of an aortic valve; and, and t is the time to opening of aortic valve.

Furthermore, in accordance with some embodiments of the present invention, said at least one cardiac function parameter is systemic vascular resistance, and wherein the processing unit is configured to determine the systemic vascular resistance by comparing a theoretical portion of an isovolumetric pressure function with an empirical central aortic pressure function.

Furthermore, in accordance with some embodiments of the present invention, the device configured to export data to a monitoring unit.

There is further provided, in accordance with some embodiments of the present invention, a device for determining a cardiac function parameter, the device including a sonic sensor for determining timing data of the closure of the mitral and aortic valves, a pressure sensor configured to be positioned within a central aorta of a patient for sensing pressure data during a pressure build-up within the central aorta, and a processing unit for determining a value of at least one cardiac function parameter based on the data.

Furthermore, in accordance with some embodiments of the present invention, the sonic sensor is a microphone.

Furthermore, in accordance with some embodiments of the present invention, the device configured to export data to a monitoring unit.

Furthermore, in accordance with some embodiments of the present invention, said at least one cardiac function parameter is selected from the group of cardiac function parameters consisting of end diastolic pressure, max dP/dT, isovolumetric contraction time, systemic vascular resistance, and central aortic pressure.

Furthermore, in accordance with some embodiments of the present invention, said at least one cardiac function parameter is systemic vascular resistance, and wherein the processing unit is configured to determine the systemic vascular resistance by comparing a theoretical portion of an isovolumetric pressure function with an empirical central aortic pressure function.

There is further provided, in accordance with some embodiments of the present invention, a method for determining a cardiac function parameter, the method including collecting timing data of the closure of the mitral and aortic valves using a sonic sensor, using a sensing unit coupled to a pressure cuff, for sensing. The sensing including for each cardiac cycle, blood breakthrough pressure data and corresponding time data from the closing of the mitral valve and data relating to a velocity of propagation of a pressure wave as it travels along at least a portion of the pressure cuff. And, determining a value of at least one cardiac function parameter based on the data, using a processing unit.

Furthermore, in accordance with some embodiments of the present invention, said at least one cardiac function parameter is selected from the group of cardiac function parameters consisting of end diastolic pressure, max dP/dT, isovolumetric contraction time, systemic vascular resistance, and central aortic pressure.

Furthermore, in accordance with some embodiments of the present invention, said at least one cardiac function parameter is max dP/dT, and wherein the processing unit is configured to iteratively calculate cardiac pressure and related values by calculating the slope of the tangent to a pressure waveform at a time point where the aortic valve opens.

Furthermore, in accordance with some embodiments of the present invention, said at least one cardiac function parameter is max dP/dT, and wherein the processing unit is configured to calculate an integral of a second derivative of a polynomial function.

Furthermore, in accordance with some embodiments of the present invention, wherein said at least one cardiac function parameter is an end diastolic pressure, and wherein the processing unit is configured to calculate the end diastolic pressure using the equation:

$$pov = \left(\frac{1}{2} \times \frac{\max \frac{dP}{dT}}{\omega}\right) \times (1 - \cos(\omega t)) + EDP$$

where:
pmax is the pressure that a isovolumetrically contracting left ventricle would produce from the end diastolic volume if ejection of blood from the ventricle would be prevented; max dP/dT is the maximum isovolumetric pressure rate in the left ventricle; ω is the angular frequency; EDP is an end diastolic pressure value; pov is the pressure at opening of an aortic valve; and, and t is the time to opening of aortic valve.

Furthermore, in accordance with some embodiments of the present invention, said at least one cardiac function parameter is systemic vascular resistance, and wherein the processing unit is configured to determine the systemic vascular resistance by comparing a theoretical portion of an isovolumetric pressure function with an empirical central aortic pressure function.

There is further provided, in accordance with some embodiments of the present invention, a device, the device including an infusion pump and a plurality of outputs, the outputs configured to release one or a plurality of agents in response to changes in LVEDP.

There is further provided, in accordance with some embodiments of the present invention, a method of stabilizing a patient, the method including using an infusion pump with a plurality of outputs, the outputs configured to release one or a plurality of agents in response to changes in the patient's LVEDP.

There is further provided, in accordance with some embodiments of the present invention, a method for predicting ischemia, the method including iteratively empirically determining values related to heart pressure at the brachial artery using a brachial cuff, iteratively mathematically deriving values relating to blood pressure at the aorta, iteratively calculating max dP/dT, iteratively calculating one or a plurality of changes in max dP/dT, determining, via a processor, whether the one or a plurality of changes of max dP/dT is indicative of ischemia, and. outputting via an output whether the one or a plurality of changes of max dP/dT is indicative of ischemia.

There is further provided, in accordance with some embodiments of the present invention, a device for predicting ischemia, the device including an input, the input configured to relay iteratively empirically determined values related to blood pressure at the brachial artery to a processor, the processor configured to iteratively mathematically deriving values relating to heart pressure at the aorta, iteratively calculate max dP/dT, iteratively calculate one or a plurality of changes in max dP/dT, and, determine whether the one or a plurality of changes of max dP/dT is indicative of ischemia, and, an output configured to output whether the one or a plurality of changes of max dP/dT is indicative of ischemia.

There is further provided, in accordance with some embodiments of the present invention, a method for mathematically deriving values relating to heart pressure at the aorta, the method including, collecting empirical data relating to brachial blood pressure via a brachial cuff wherein the empirical data can be plotted on a polynomial function to describe brachial blood pressure, mathematically deriving a delay value representing the time shift between the polynomial function describing the brachial blood pressure and a polynomial function describing blood pressure at the aorta, and, computing via a processor the polynomial function describing blood pressure at the aorta using the collected empirical data and the mathematically derived delay value.

There is further provided, in accordance with some embodiments of the present invention, a device for mathematically deriving values relating to heart pressure at the aorta, the device including an input for collecting empirical data relating to brachial blood pressure wherein the empirical data can be plotted on a polynomial function to describe brachial blood pressure, a processor for mathematically deriving a delay value representing the time shift between the polynomial function describing the brachial blood pressure and a polynomial function describing blood pressure at the aorta and for computing via a processor the polynomial function describing blood pressure at the aorta using the collected empirical data and the mathematically derived delay value, and, an output for outputting data derived from the polynomial function describing blood pressure at the aorta.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

Figure 1:
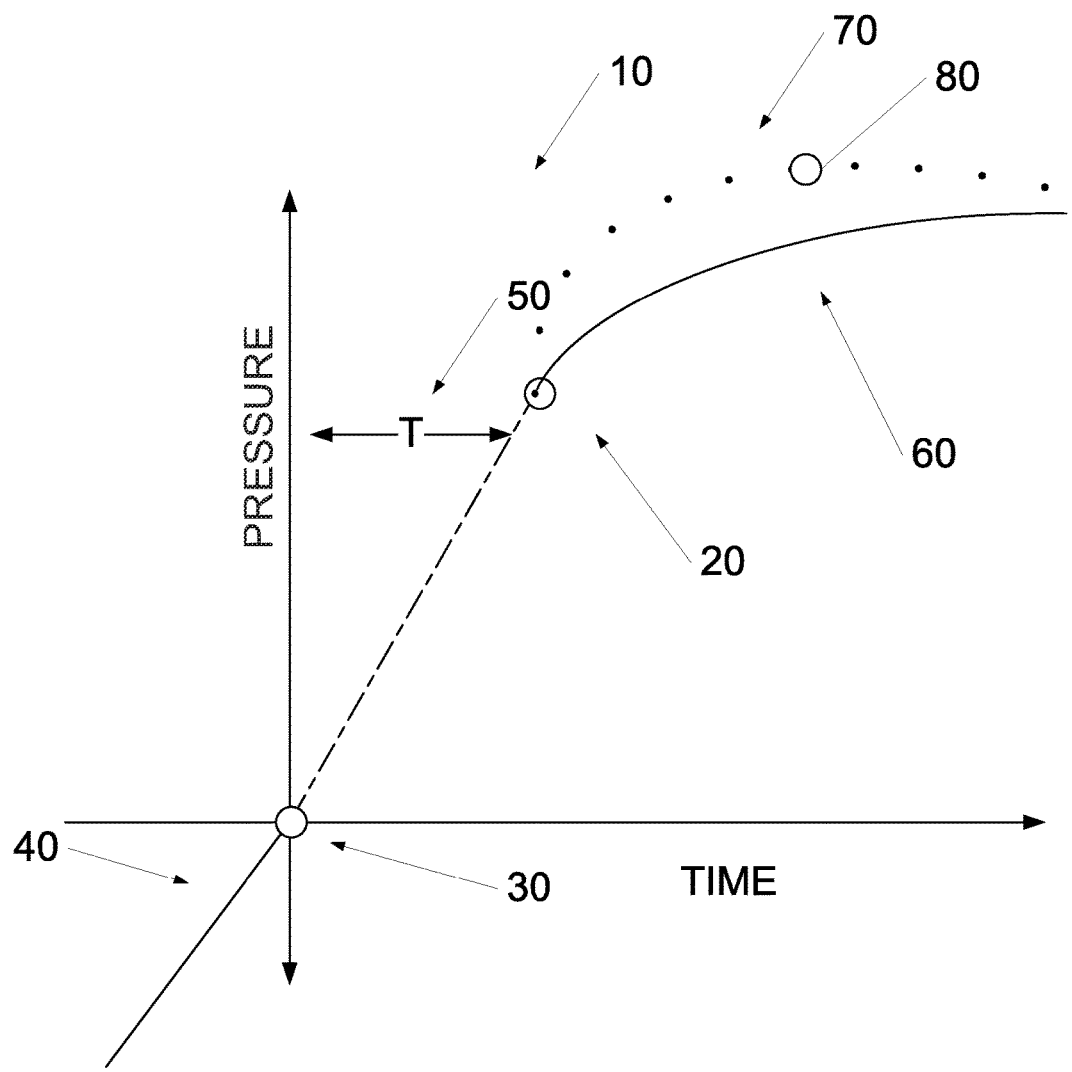
FIG. 1 is a graph representing a cardiac pressure curve over time that may be used for understanding and non-invasively determining ventricular pressure and related values, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the methods and apparatus. However, it will be understood by those skilled in the art that the present methods and apparatus may be practiced without these specific details. In other instances, well-known methods, procedures, and components have not been described in detail so as not to obscure the present methods and apparatus.

Although the examples disclosed and discussed herein are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method examples described herein are not constrained to a particular order or sequence. Additionally, some of the described method examples or elements thereof can occur or be performed at the same point in time.

Unless specifically stated otherwise, as apparent from the following discussions, it is appreciated that throughout the specification, discussions utilizing terms such as "adding", "associating" "selecting," "evaluating," "processing," "computing," "calculating," "determining," "designating," "allocating" or the like, refer to the actions and/or processes of a computer, computer processor or computing system, or similar electronic computing device, that manipulate, execute and/or transform data represented as physical, such as electronic, quantities within the computing system's registers and/or memories into other data similarly represented as physical quantities within the computing system's memories, registers or other such information storage, transmission or display devices.

Central aortic pressure or central aortic blood pressure refers to blood pressure at the root of the aorta where it connects to the heart. The determination of central aortic pressure and ventricular pressure are important components in treating heart disease and related concerns. Whereas traditional non-invasive methods of determining blood pressure rely on blood pressure cuffs and similar devices, these measurements often underestimate and/or overestimate efficacy of some cardiovascular treatments and pharmacological efforts.

A non-invasive methodology of determining ventricular may be a component in determining, noninvasively, other significant values within the cardiac cycle, and other cardiac function parameters.

FIG. 1 is a graph representing a cardiac pressure curve, plotted over a time period; the curve is useful for understanding a noninvasive determination of ventricular pressure and related values according to an embodiment of the invention. The plot is presented for illustrative purposes and may not be representative of the shape of a known cardiac pressure curve.

Ascending aortic pressure, at the time point of the opening of the aortic valve, is equal to the pressure of the left ventricle. The device described below may measure the aortic pressure at this temporal point, this measurement may be used to determine the peak ventricular pressure.

The graph 10 depicts cardiac pressure, measured, in mmHg on the Y axis. Graph 10 depicts a measure of time over the course of a cardiac cycle on the X axis; the measurement of time is in milliseconds.

The origin of graph 30 represents the point within the cardiac cycle defined as the end diastolic pressure, or left ventricle end diastolic pressure (LVEDP). LVEDP, or peak ventricular pressure, may be an expression of Startling's Law whereby the force of contraction of the cardiac muscle is a function of the initial fiber length at end diastolic volume or heterometric autoregulation.

In some embodiments of the invention, a measurement of the time 50 (T) it takes for pressure to build up in the left ventricle, without a change in ventricular volume, may be determined, i.e., the isovolumetric contraction time (IVCT). IVCT is specific to each individual person and may vary over a lifetime. IVCT may be used not only to determine the slope of the curve that may provide additional diagnostic information, but it, in of itself, may be useful as a diagnostic tool.

IVCT may have diagnostic value as it may be seen as a direct expression of the sum of factors that comprise contractility of the heart muscle. Changes in IVCT may reflect changes in electric, neural, metabolic and pharmacological influences on the heart and its component parts.

IVCT may also be defined as the period of left ventricular mural tension in addition to the period of rising cavitary pressure within the left ventricle. Physiologically, IVCT ends when intraventricular pressure exceeds aortic pressure; the resulting pressure gradient opens the aortic valve and ejection of blood into the aorta quickly reduces ventricular volume.

The IVCT refers to a time period during systole, or right before the beginning of systole 60. Cardiac function during systole may be plotted as a portion of an empirically determined central aortic pressure function, as determined by iteratively plotting pressure values collected by a pressure cuff against time.

The beginning of systole may be defined, in terms of cardiac pressure values, at the point in time of the cardiac cycle defined as LVEDP, and/or right after the end of diastole 40. This temporal period may coincide with the closing of the mitral valve and or other cardiac valves, for example the tricuspid valve. Graph 10 is normalized such that systole, as defined in some instances, begins at origin 30, and origin 30 coincides with LVEDP. In some examples, IVCT may precede mitral closure.

LVEDP may be defined anatomically as referring to the isovolumetric contraction wherein the mitral and tricuspid valves are closed (i.e., the lub sound in the heart beat), resulting in the contracting of the heart ventricles, and wherein pressure within the ventricles begins to rise as the blood volume remains constant.

IVCT may be further described as ending at the subsequent opening of the semilunar aortic valve and pulmonary valves, and the rapid ventricular ejecting of blood through the aorta and pulmonary artery. Once the semilunar valves close, ventricular pressure may rapidly drop, resulting in the closing of the aortic valve (the dub sound in the heart beat).

This IVCT may additionally be definable as a temporal period between the temporal point defining LVEDP and the temporal point in the cardiac cycle defined as max dP/dT 20, i.e., the maximum isovolumetric pressure rate, e.g. the maximum rate of the rise of left ventricular pressure, the value related to the speed in which ventricular muscle can compress blood until it hits an ejection point.

The value of max dP/dT, specific for each person, may be useful clinically to characterize the contractilability of the heart. In general, dP/dT may reflect, in certain clinical conditions, the inotropic state of the heart, i.e., the contractibility of cardiac muscle tissue. In some examples, this value may be irrespective and/or independent of ventricular morphology, localized wall motion abnormities, and/or structural abnormalities within the heart.

Ventricular max dP/dT may also be related to aortic max dP/dT, albeit occurring in different phases, where aortic max dP/dT occurs while ventricular dP/dT is decreasing from its maximum. Thus, the value of max dP/dT may also be indicative of the initial velocity of blood through the aorta at the end of the myocardial contraction.

Max dP/dT may also be related to pmax 80, where pmax is the pressure that the isovolumetrically contracting left ventricle would produce from the end diastolic volume if ejection of blood from the ventricle would be prevented.

That is, pmax is the product of max dP/dT and the systolic cycle length where:

$$p\max = \frac{\max dp/dt \times \tau}{\pi},$$

where τ is the time measured from the occurrence of the end of the diastolic pressure until the same pressure is reached during the descending portion of isovolumetric relaxation.

pmax, the peak isovolumetric pressure, may be an estimation of the output pressure of the left ventricle, considered in engineering terms the hydromotive source pressure.

LVEDP is a significant diagnostic value. An elevated LVEDP may be associated with dysfunction of the left ventricle: patients with symptoms of heart failure and normal ejection fraction will present an increased left ventricular end-diastolic pressure. Elevated LVEDP could be associated with systolic but also diastolic dysfunction. Elevated left ventricular end-diastolic pressure may also be a risk factor in cardiac surgery.

Elevated LVEDP may also be commonly associated with reduced left ventricular function, a risk factor for post cardiac surgery mortality. Elevated LVEDP may also indicate left ventricular hypertrophy. Elevated LVEDP may also be associated with filling/loading abnormalities.

In some embodiments of the invention, values for the pressure curve may be derived non-invasively. In some embodiments of the invention, this may include applying occluding pressure to an artery, in some examples, the brachial artery. Other arteries may also be occluded in other embodiments of the invention.

While pressure is applied against the brachial artery, time may be plotted in the pressure graph described above, noting the first instance wherein the aortic pressure wave equalizes and brakes through the occlusive pressure at the brachial artery level, the occlusive pressure provided at a known distance from the aorta.

In some embodiments of the present invention, the externally applied pressure that result in the occlusion of the brachial artery e.g., a sphygmomanometer arm cuff or pressure cuff, and the closure of the aortic valve, may together result in a condition that may resemble a standing fluid column. The standing fluid column may reflect a rising intercavitary pressure that is homogenously transmitted to the periphery of the body from the heart.

The time necessary for the pressure wave of blood from ejection into the aorta to the point of occlusion in the brachial artery may be equal with the time intervals needed to reach the same pressure in the central aorta added to the time necessary to propagate to the brachial pressure point.

In some examples, a velocity of propagation of blood through the aorta and the peripheral artery may be calculated through the use of a sensing unit described below in the pressure cuff. The sensing unit may include one or a plurality of sensors, the sensors configured to measure the pressure applied by the cuff to the peripheral artery. In some examples, the sensing unit may include a Doppler sensor. The Doppler sensor may be configured to collect blood breakthrough pressure data, e.g., collect data related a breakthrough of blood past a constricted artery. In some examples, the sensing unit may include one or a plurality of sensors configured to determine the velocity of propagation of blood. In some examples two sensors may be placed at a known distance from each other on the pressure cuff, for example 3-10 cm, e.g., 5 cm from each other on the pressure cuff. The passage of time from a first sensor to a second sensor as blood flows through an artery underneath the pressure cuff may provide data for determining the velocity of propagation.

For example, this result may be accomplished by measuring the time delay between the R wave on an electrocardiogram and a brachial pulse during gradual deflation of a pressure cuff.

In some examples the velocity of propagation and data relating to the distance of the sensing unit from the aorta can provide data for determining cardiac function parameters.

In some examples the sensing unit on the pressure cuff may be employed to iteratively determine pressure values with respect to time. These values may be used to create a portion of a waveform graph, e.g., a portion of the graph in FIG. 1 that includes an empirically derived central aortic pressure function. An isovolumetric pressure function may be represented as a line between the origin on graph 10 and max dP/dT. Depicted in FIG. 1 as a hashed line.

In some examples, a stethoscope or other listening device may be employed to listen for the breakthrough of arterial blood flow, through the formerly occluded artery, at the site of a deflating pressure cuff or sphygmomanometer arm cuff. In some examples, one or a plurality of sensor devices, including Doppler sensor devices, may be used to determine the first brachial artery flow past the deflating cuff.

In some examples, the sphygmomanometer arm cuff may have an additional sensor, e.g., a Doppler sensor which detects arterial blood flow. Using the Doppler sensor a user may be able to detect with a degree of accuracy the different breakthroughs of arterial blood flow past the deflating cuff: while the sphygmomanometer arm cuff slowly diminishes the pressure its exerts the detection of the renewed blood flow through the blocked artery may be done with the Doppler sensor and the pressure measurement may be done using one or a plurality of pressure sensors in the sphygmomanometer arm cuff.

In some examples, a pressure sensor may be employed with the pressure cuff to measure the pressure of the deflating cuff against the peripheral artery.

In some embodiments of the invention, a processing unit, e.g., a computing device, may employ algorithms and command and control features to the pressure cuff and sensors, including a listening device to better determine the above-mentioned values and to minimize artifacts and to maximize consistency within readings.

In some examples, the processing unit may be connected to a terminal, monitor, LCD, computer, the internet, the Cloud, or other computing peripheral, display or printing device.

The data may provide sufficient information to reconstruct an ascending limb of the systolic pressure wave within the cardiac cycle.

In some examples, a reconstructed ventricular pressure curve and/or an empirical central aortic pressure function may be constructed from data obtained from multiple successive occlusive pressures on the brachial artery: plotting a plurality of cuff pressure measurements against corresponding time delays between the opening of the aortic valve and the sensed blood-flow breakthrough from multiple cardiac cycles. In some embodiments of the invention, calculating these and/or additional values may provide for the construction and/or generation of the ascending arterial pressure waveform, plotting pressure in mm HG over time, in some examples in milliseconds.

Typically distorting factors may not be present in these measurements including blood viscosity, mass, vasoconstriction of the arterial path and other possibly distorting factors.

Data may be calculated and/or plotted as pressure varying with time, obtained with time being a function of declining pressure exerted at the brachial artery by the sphygmomanometer arm cuff. A graph of these values may display pressure increasing than decreasing with respect to time. Systolic pressure may be the maximal pressure values, in some examples the point with the longest time delay. Diastolic pressure may be taken at the inflection point of the pressure curve.

The diastolic pressure, i.e., the point of max dP/dT, may be calculated by finding a tangent to the waveform function. The slope of the tangent, e.g., the first derivative of the waveform function—the waveform function the result of non-linear least square analysis to find the coefficient of a fourth degree polynomial, i.e., a quartic equation, will provide a user with the maximal rate of change of isovolumetric pressure: the first derivative of the waveform function, at the point of the graph relating to the temporal point of the opening of the aortic valve may be defined as the max dP/dT.

The derivative the waveform function may describe the best linear approximation of the function near that input value and equal to the slope of the tangent line to the graph of the waveform function at max dP/dT.

A second method to determine max dP/dT, in some embodiments of the invention, a method that may be less sensitive to noise, may use the integral of the second derivative of the waveform function from the temporal period wherein the aortic opens until the peak aortic pressure, the waveform function described above. The second derivative may reflect how max dP/dT, is itself changing. The taking of the integral of the second derivative under the entire curve allows for an estimation of max dP/dT with less concern for small empirical error.

Graph 10 may, in some examples, be phase shifted, and/or normalized, to have diastolic pressure begin, e.g., the onset of the ejection process, at the origin.

In some embodiments of the invention a reconstructed ventricular pressure curve and/or an empirical central aortic pressure function, described below may be compared with the theoretical portion of an isovolumetric function 70, the theoretical portion, here displayed as a dotted line, which may behave as a cosine function, may contain the pmax value described above. A comparison of the two curves and/or functions may provide indications and parameters related to systemic vascular resistance (SVR), where SVR may refer to blood flow resistance offered by the systemic vasculature of a subject, excluding specifically the pulmonary vasculature (i.e., pulmonary vascular resistance).

In some embodiments of the invention, the change in slope of the pressure waveform after max dP/dT 20 may be indicative of a change in peripheral arterial resistance to blood flow. This change in peripheral resistance may be directly related to the determination of vasodilatation in one or a plurality of arteries of a patient.

The determination of vasodilatation may be relevant for determine the efficacy of a class of drugs or for determining a disease state.

In some examples, a drug could be provided, for example, a vasodilator, and measurements could be taken to determine the extent to which vasodilatation has occurred and/or the resistance to flow in the dilated arterial blood vessels. The dilation may be to decrease blood pressure, to treat hypertension, angina or congestive heart failure, or to increase tissue perfusion of for other therapeutic benefits.

In some embodiments of the invention, the relationship between peak isovolumetric pressure (max) and end-diastolic volume can indicate ventricular contractility.

A practical method to estimate pmax may be from the pressure curve of an ejecting contraction of left ventricle and may be used to estimate pmax from a single ejecting beat.

The difference between the estimated value pressure values, where the estimated value may be corrected for physiological considerations including the percentage volume ejected from the ventricle and the values read by a blood pressure cuff may indicate changes in resistance of the arterial vessels, for example, as a result of vasodilatation.

From the calculation of max dP/dT, the value may be incorporated into the equation where peak isovolumetric pressure could be mathematically predicted by curve-fitting isovolumetric data from an ejecting beat to a cosine function, the equation representing a nonlinear least squares approximation technique developed by Sunagawa et al.

$$\text{The Isovolumetric pressure curve} = \frac{1}{2} p \, \text{max} \times (1 - \cos(\omega t)) + EDP$$

Where $\omega$ is the angular frequency and/or where $$\omega = \frac{2\pi}{SystolicTime}.$$

And where, EDP is the LVEDP, as described above.

The isovolumetric pressure curve may be obtained by fitting the measured EDP curve segments from the end-diastolic pressure point to the max positive dP/dT, and from the pressure point of the negative max dP/dT, to the same level as the end-diastolic pressure of the preceding heart beat. And wherein the peak of the ECG R wave may be used to identify the LV end-diastolic point.

With these values, the equation may be rewritten as:

$$\frac{1}{2} p \, \text{max} - \frac{1}{2} p \, \text{max}(\omega t)) + EDP.$$

The derivative of the equation may be calculated to be:

$$-\frac{1}{2} p \, \text{max} \times \omega \times -\sin(\omega t).$$

Under the conditions described above, at max dP/dT, $\sin(\omega t)=1$ at point t, where t is the opening of aortic valve. Thus, max $dP/dT = p \, \text{max}(\omega)$; or $$p \, \text{max} = \frac{\text{max} \frac{dP}{dT}}{\omega}$$

Both the hydromotive pressure calculated by the equation above and the aortic pressure pass through the same point at opening of aortic valve i.e. the pressure in the left ventricle at max dP/dT is equal to the pressure in the aorta at the same time one can use the following equation:

$$pov = \left(\frac{1}{2} \times \frac{\text{max} \frac{dP}{dT}}{\omega}\right) \times (1 - \cos(\omega t)) + EDP$$

where pov is the pressure at opening of aortic valve, a value that may be empirically measured;

and t is the time to opening of aortic valve a value that may be empirically measured.

The equation may be rewritten $$EDP = pov - \left(\frac{1}{2} \times \frac{\text{max} \frac{dP}{dT}}{\omega}\right) \times (1 - \cos(\omega t))$$

Allowing for the non-invasive derivation of EDP (LVEDP).

The experimental determination of max dP/dT, LVEDP, and a change in peripheral resistance may provide for a comprehensive picture and understanding of the whole hemodynamic system of the heart.

Figure 2A:
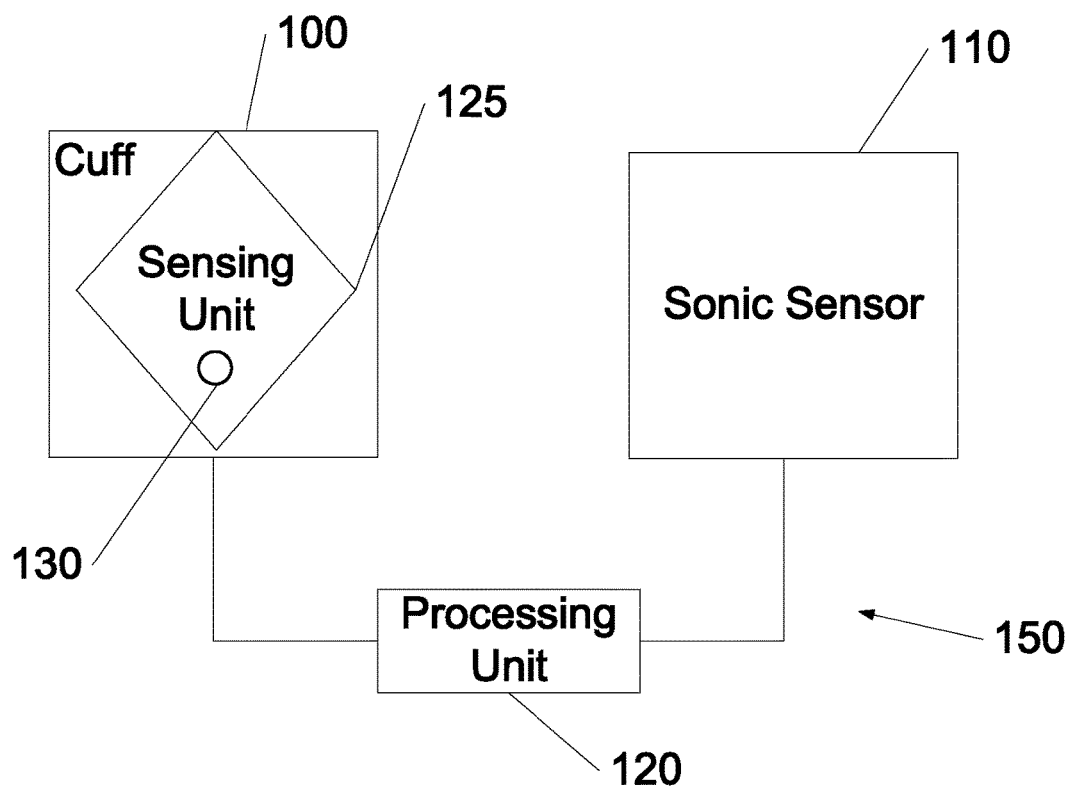
FIG. 2a is schematic illustration of a method that may be used for understanding and non-invasively determining ventricular pressure and related values, according to an embodiment of the invention.

FIG. 2a is schematic illustration of a device 150 for the noninvasive determination of ventricular pressure and related values according to an embodiment of the invention.

Device 150 may include a pressure cuff 100 or another device configured to apply pressure. The pressure may be applied to create a temporary occluded peripheral artery. For example, a sphygmomanometer arm cuff may be used to apply pressure to an artery, for example, the brachial artery and then slowly release pressure to the artery. Other devices may also be employed.

In some embodiments of the invention there may be a sensing unit 125. Sensing unit 125 may include one or a plurality of sensors. In some examples, one or a plurality of sensors may be blood flow sensors 130. The blood flow sensors may be coupled directly or indirectly to pressure cuff 100. The blood flow sensors may be coupled to a portion of pressure cuff 100.

Blood-flow sensors 130 may be configured to measure the velocity of the blood flow in an artery, e.g., the velocity of the propagation of the pressure wave of blood travelling through the arteries. Blood flow sensors 130 may be configured to be employable for obtaining diverse values related to blood flow through the artery. Sensing unit 125 may also include pressure sensors. Pressure sensors may determine the pressure, in some examples measured in mmHg, of the pressure cuff when a blood flow breaks through occurs.

Other sensors may also be employed to provide accurate readings regarding the first breakthrough of blood through the brachial artery. Sensors within sensing unit 125 may be configured to provide time data, the time data may correspond to a temporal period, that temporal period starting at the time of the closure of a heart valve, e.g., the mitral valve.

Sensing unit may include Doppler sensors to determine, in some embodiments of the invention, a blood flow breakthrough.

In some embodiments of the invention, a first blood sensor may be configured to record macro readings and a second blood flow sensor 130 may be configured to record micro, e.g., more precise readings. In some embodiments of the invention, two or more sensors may be used given expected broad ranges of activities that may be sensed in the cuff.

In some embodiments of the inventions, two sensors may be employed to correct for the interval between pressure rise in aorta and subsequent pressure rise in the brachial artery. The two sensors may be employed to calculate the speed of a pressure wave as it travels through the peripheral artery.

In some embodiments of the invention, the blood-flow sensors 130 may be configured to iteratively determine and record the time and corresponding cuff pressure, e.g., the occlusive pressure values of the initial blood flow breakthrough past the deflating pressure cuff 100 through a peripheral artery, e.g., the brachial artery. In some examples, these values may be employed by processing unit to create a function representative of the central aortic pressure and/or other cardiac function parameters.

A sonic sensor 110 may be configured to detect heart muscle activity, for example the closing of a heart valve, e.g., the aortic and/or mitral valves. In some examples a non invasive heart sensor, for example a microphone, may be configured to determine the values relating to the beating of the heart and the ejection of blood from the ventricle into the aorta.

In some embodiments of the invention, sonic sensor 110 may be an audio device configured to listen to audio sounds, e.g. for cardiac auscultation, emanating from the heart, the sounds indicative of physiological changes in the heart. The sounds may be employed in determining systolic time. A first sound may be a closing of a mitral valve once blood has entered the ventricular chamber. ($S_1$, e.g., the 'lub' sound). In some embodiments of the invention, the audio device may be configured such that whereas the $S_1$ sound may heard as a single sound, the audio device may be configured such that it can differentiate between the sound resulting from the mitral valve closure and the sound of the latter tricuspid valve closure.

And second sound, the second sound indicative of isovolumetric relaxation. The second sound may be the closing of the aortic valve once the ejection of volume from the ventricular chamber has occurred. ($S_2$, e.g., the 'dub' sound) In some embodiments of the invention, the audio device may be configured to distinguish between the sound resulting from the closure of the aortic valve and the subsequent closure of the pulmonary valve, the difference in time between the two closures may vary considerably depending on respiration, posture or pathological conditions.

By determining S1 and S2 with a degree of accuracy, the device may allow for the obtaining of the duration of systole. The duration of systole may be a variable to be included in the computational analysis described below.

In some examples the invention may include an Electrocardiogram (ECG) device. The ECG may be configured to provide an interpretation of the electrical activity of the heart over a period of time, as detected by electrodes attached to the outer surface of the skin and recorded by a device external to the body. The ECG may also be employed to measure the rare and regularity of the heartbeats, In some examples, max dP/dT may coincide with an ECG R wave and may occur shortly after an ECG Q wave.

Doppler echocardiography devices may also be used.

A processing unit 120 may include processing components, memory components and other components related to processing. The Processing unit may include processors that may employ algorithms to control and monitor device 100, sonic sensor 110, and blood-flow sensor 130. Processing unit 120 may include a screen for displaying graphically an arterial wave with relevant data points highlighted. Processing unit 120 may include a method for printing out values and graphs relating to the relevant curves, waves and data units.

Processing unit 120 may be configured to determine one or a plurality of values for at least one cardiac function parameter based on the data, the data typically collected by sensing unit 125 and/or sonic sensor 110.

Processing unit 120 may include components for wired and/or wireless communication. The wired and/or wireless communication may be with pressure cuff 100, sonic sensor 110, and/or blood-flow sensor 130. Processing unit 120 may be coupled to pressure cuff 100, sonic sensor 110, and/or blood-flow sensor 130.

Device 150 may be configured to determine from values collected by device 100, sonic sensor 110, and blood-flow sensor 130 and/or processing unit 120 additional cardiac related values. In some embodiments of the invention, device 150 may determine total peripheral resistance. In some examples, the total peripheral resistance may be a function of the area under the pressure waveform, subsequent to max dP/dT.

The device allows for the noninvasive determination of the isovolumetric contraction time, wherein the beginning of the pressure curve is in fact may correspond with physiological opening of the aortic valve. The opening of the aortic valve is typically acoustically silent, and is typically otherwise determined via echocardiography.

Device 150 may be configured to determine systemic vascular resistance in a subject as described above.

Device 150 may be configured to be connected to a monitoring unit. Data and/or output from device 150 may be displayed using a display methodology such as a monitor, printer or other display methodology that may be exclusive to device 150 or may be shared with and/or exported to other devices, e.g., a monitoring unit within a hospital, home or clinical setting, the monitoring unit may be configured to display and/or otherwise communicate other cardiac or health related data. Export data from device 150 may also be displayed on the monitoring unit.

Figure 2B:
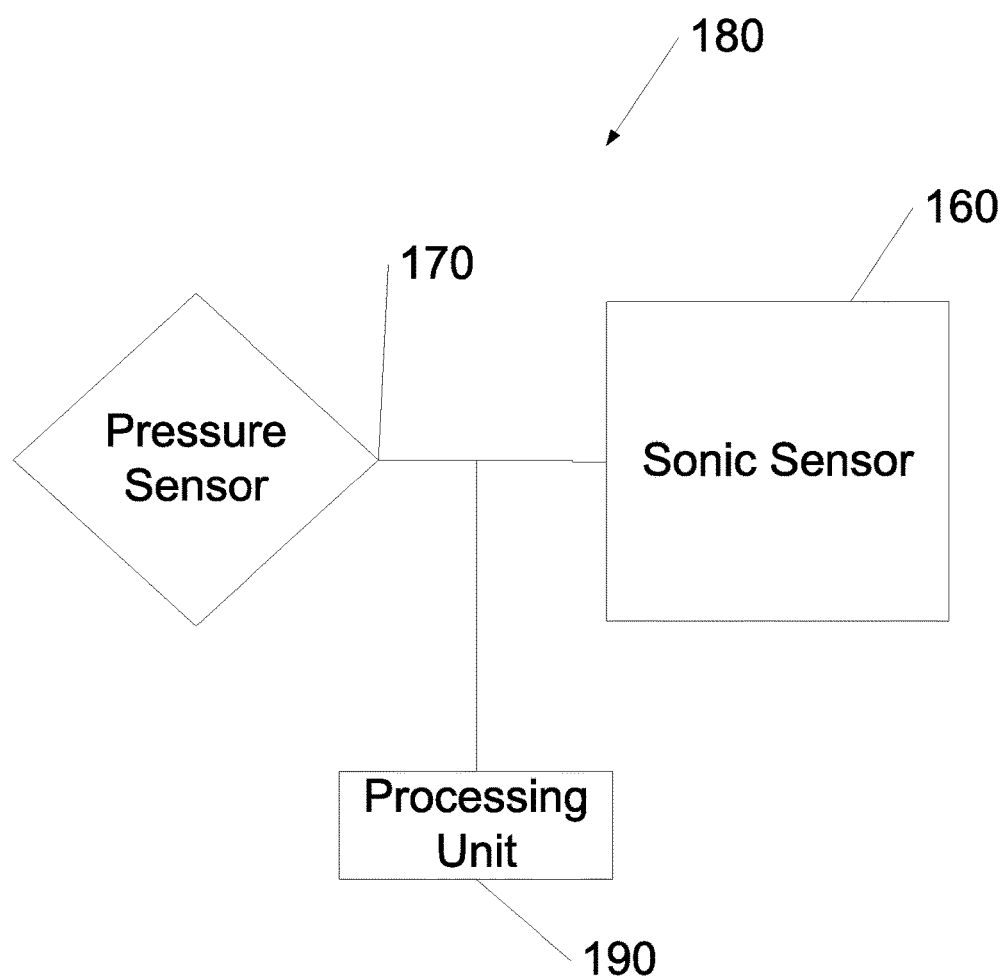
FIG. 2b depicts a schematic illustration of a minimally invasive device for determination of ventricular pressure and related values according to an embodiment of the invention.

FIG. 2b depicts a schematic illustration of a minimally invasive device for determination of ventricular pressure and related values according to an embodiment of the invention.

In some embodiments of the invention, a device 180 may include a sonic sensor 160. Sonic sensor may be configured to determine timing data related to the closure of the mitral and aortic valves, the closures of the valves making the characteristic "lub" and "dub" sounds that may be picked up and accurately and timely recorded via the sonic sensor.

In some embodiments of the invention, device 180 may include a pressure sensor unit 170 may be positioned within a central aorta of subject or patient. In some embodiments of the invention, the pressure sensor unit 170 may be placed elsewhere within the patient's body.

In some embodiments of the invention, sensing unit 170 may be configured to sense pressure data during a pressure build-up within the central aorta or other components of the cardiac system.

A processing unit 190 may be configured to determine the value of one or a plurality of cardiac unction parameters based on the data from sensing unit 170 and sonic sensor 160. Other sensors may also contribute data.

Figure 3:
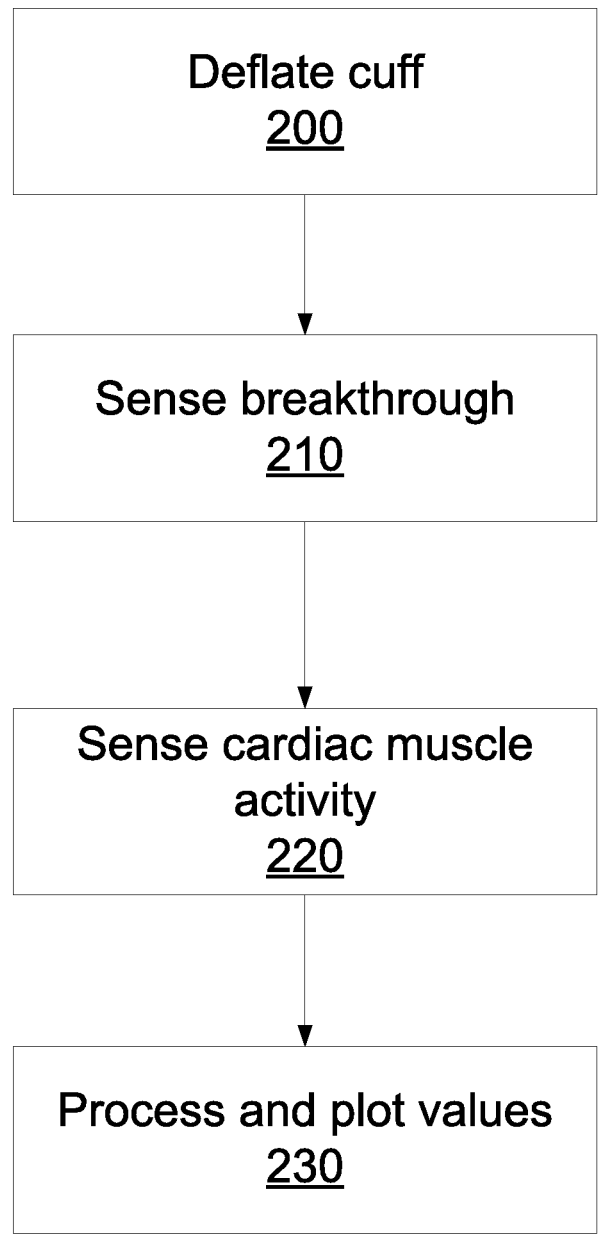
FIG. 3 is a schematic diagram of a method that may be used for understanding and non-invasively determining ventricular pressure and related values, according to an embodiment of the invention.

FIG. 3 is a schematic diagram of a method for the noninvasive determination of ventricular pressure and related values according to an embodiment of the invention.

The method for noninvasively determining max dP/dT, isovolumetric time and end diastolic pressure, from a peripheral artery according to an embodiment of the invention, may include configuring a pressure cuff to deflate as depicted by box 200.

Box 210 depicts the configuring one or a plurality of sensors coupled to the cuff to determine an initial blood flow breakthrough on a patient or subject.

Box 220 depicts the configuring a sonic sensor to determine the opening of an aortic valve.

Box 230 depicts the configuring a processing unit to measure, process and/or plot occlusive pressures values applied to a peripheral artery against time intervals as determined by the one or a plurality of sensors and the heart sensor.

Figure 4:
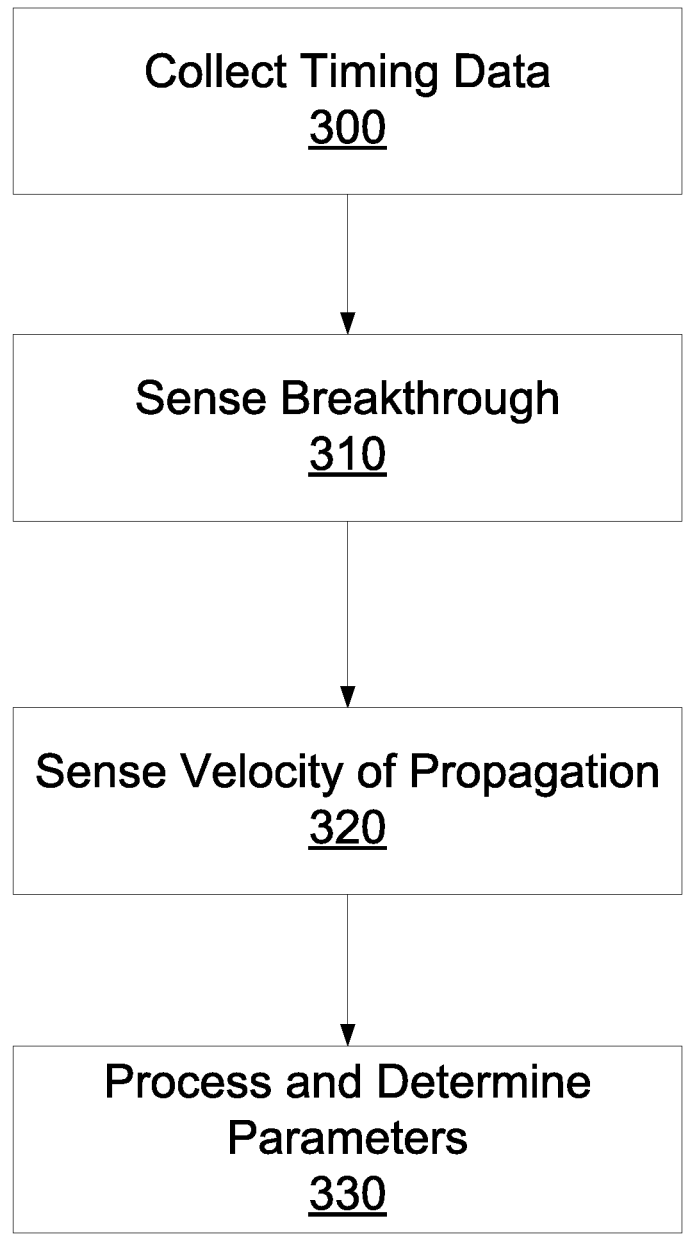
FIG. 4 is a schematic diagram of a method that may be used for understanding and non-invasively determining ventricular pressure and related values, according to an embodiment of the invention.

FIG. 4 is a schematic diagram of a method for determining a cardiac function parameter according to an embodiment of the invention.

As depicted in box 300, the method includes collecting timing data of the closure of the mitral and aortic valves using a sonic sensor.

Box 310 depicts using a sensing unit coupled to a pressure cuff to sense, for each cardiac cycle, blood breakthrough pressure data and corresponding time data from the closing of the mitral valve.

Box 320 depicts using the sensing unit to collect data; in some examples, the sensing unit may be coupled to the pressure cuff. In some embodiments of the invention the sensing unit may include numerous separate sensors where some of the sensors may be coupled to portions of the sensor cuff and other sensors may be coupled to other portions of the cuff, or may be separate from the sensor cuff. The sensing unit may be configured to sense data relating to a velocity of propagation of a pressure wave as it travels along at least a portion of the pressure cuff.

A processing unit may be configured to determine a value of at least one cardiac function parameter based on the data, as depicted in box 330.

In some examples, the method may include configuring the processing unit to run one or a plurality of algorithms, the algorithms configured to integrate the second derivative of the $4^{th}$ degree polynomial function from a graphical representation of a arterial pressure wave, the arterial pressure wave determined empirically and extending from the opening of the aortic valve until an aortic max dP/dT, solve for $$p\max = \frac{\max\frac{dP}{dT}}{\omega}$$

and solve for EDP:

$$pov = \left(\frac{1}{2} \times \frac{\max\frac{dP}{dT}}{\omega}\right) \times (1 - \cos(\omega t)) + EDP.$$

In some examples the values that were solved for may be presented to a user visually on a screen as superimposed on a waveform. In some examples the values may be printed out. In some examples the values may be presented to a user independent of the waveform.

In some examples the processing unit may include a graphical user interface for manipulating data, sending data wirelessly or via a wired connection, manipulating graphical results and/or changing parameters of algorithms run by the processing unit.

Typically LVEDP is increased during ischemia and max dP/dT decreases during ischemia. Thus chest pain originating from an ischemic attack, such as a myocardial infarction, could be detected immediately using the values of LVEDP and max dP/dT, obtainable during a simple blood pressure type of measurement.

These two indices, being determinable noninvasively, may provide for an easier detection of ischemic heart disease including, myocardial infarction unstable angina, and other disease states, and may be used to alert the patient, who may already have risk factors for heart disease, as to impending attacks. In some examples of the invention, this information may be employed in prophylactically opening of an occluded artery at an early stage.

The determination of LVEDP and max dP/dT during a simple blood pressure type of measurement may prevent unnecessary hospitalization for chest pain of no cardiac origin.

Figure 5:
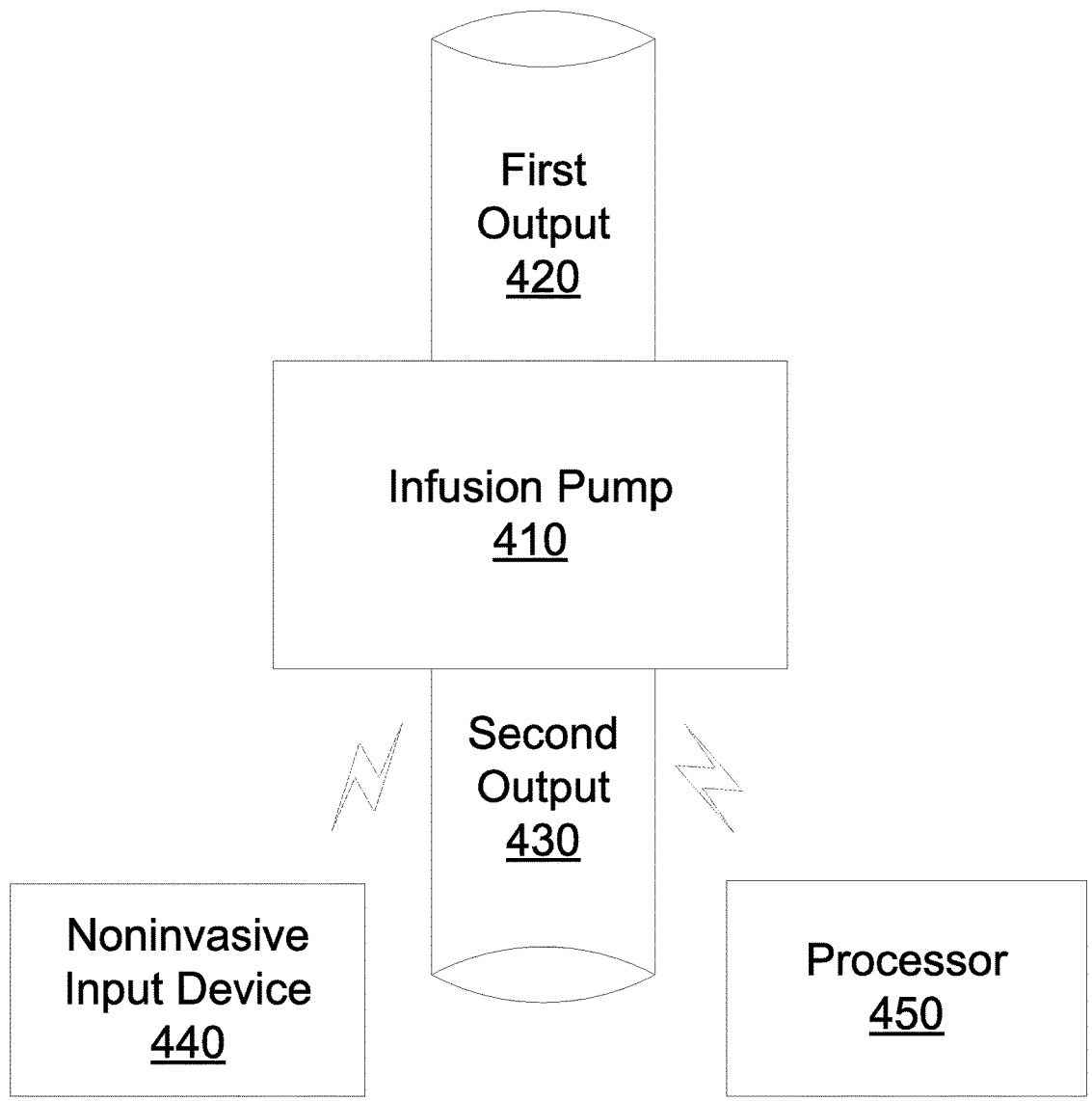
FIG. 5 is a schematic diagram of an infusion pump according to an example of the invention.

FIG. 5 is a schematic diagram of an infusion pump according to an example of the invention.

In some examples of the invention Dobutamine and/or other sympathomimetic drugs, or other drugs and/or agents can be used in a stress test. A Dobutamine infusion may be provided to a patient in conjunction with an echo-doppler scan. During an ischemic event, regional wall motion abnormalities may be detected. In some examples of where LVEDP is increased during ischemia and max dP/dT decreases during ischemia, these values detected experimentally or derived mathematically, as described, for example herein, can provide independent and/or parallel confirmation. Or, in some examples of the invention, they may be used in lieu of the Dobutamine infusion in conjunction with an echo-doppler scan.

In some examples of the invention, LVEDP can be measured as an index of heart failure exacerbation and can be used to automatically adjust treatment in patients with decompensated heart failure. Patients with congestive heart failure (CHF) and/or exacerbated CHF may be provided with doses of diuretics/vasodilatator and/or saline. In some examples, the doses of diuretics/vasodilatator and/or saline are provided via an infusion pump 410. Infusion pump 410 may have at least two outputs where a first output 420 is configured to infuse an agent such as saline and a second output 430 is configured to infuse an agent such as a diuretic or other drug into the patient.

In some embodiments of the invention, the infusion pump is connected with a noninvasive input device 440 to determine LVEDP.

When a patient's LVEDP is high, for example, if LVEDP is 30 mmHg than the diuretic output, e.g., second output 430 on infusion pump 410 may be opened and the patient may be infused with a diuretic and/or vasodilatator. The infusion of the diuretic and/or vasodilator may continue until the LVEDP, as read by a noninvasive input device 440 to determine LVEDP, reads the LVEDP value as returning to a normal healthy value, for example, 15 mmHg.

If the noninvasive inputdevice 440 determines that LVEDP values are falling then second output 430, e.g., the output for the diuretic is closed and a diuretic and/or vasodilator are no longer infused into the patient. When the second output is closed, first output 420, e.g., for infusing saline into the patient may be opened.

In some examples there may be an iterative process of opening and closing first output 420 and second output 430 until a desired blood pressure is achieved.

In some examples of the invention, a processor 450 is coupled to infusion pump 410. Processor 450, in response to data from noninvasive input device 440 to determine LVEDP may determine what outputs are opened and/or closed and the duration of the opening and closing of the outputs.

In some examples of the invention, infusion pump 410 and/or processor 450 may be implanted into the patient. Infusion pump 410 may be battery powered or powered by an external device. Infusion pump 410 may communicate wirelessly and/or via other communication methodologies with other devices, including, for example processor 450.

In some embodiments of the invention, infusion pump 410 may be a portable device that can be worn or carried by the patient. In some embodiments of the invention infusion pump 410 may be a hospital based device. In some embodiments of the invention infusion pump 410 may be a consumer device.

Noninvasive input device 440 to determine LVEDP may be directly or indirectly attached and/or in communication with the infusion pump. Infusion pump 410 may be powered by a portable battery and/or by electricity from a wall outlet.

Processor 450 may be coupled to a wireless device. Wireless device may send a signal to another device, e.g., an SMS to a physician's phone, noting a rise of fall of LVEDP.

In some embodiments of the invention, LVEDP can be derived mathematically without needing to determine the distance travelled from the point of measurement until the heart valve, for example as described above.

Figure 6A:
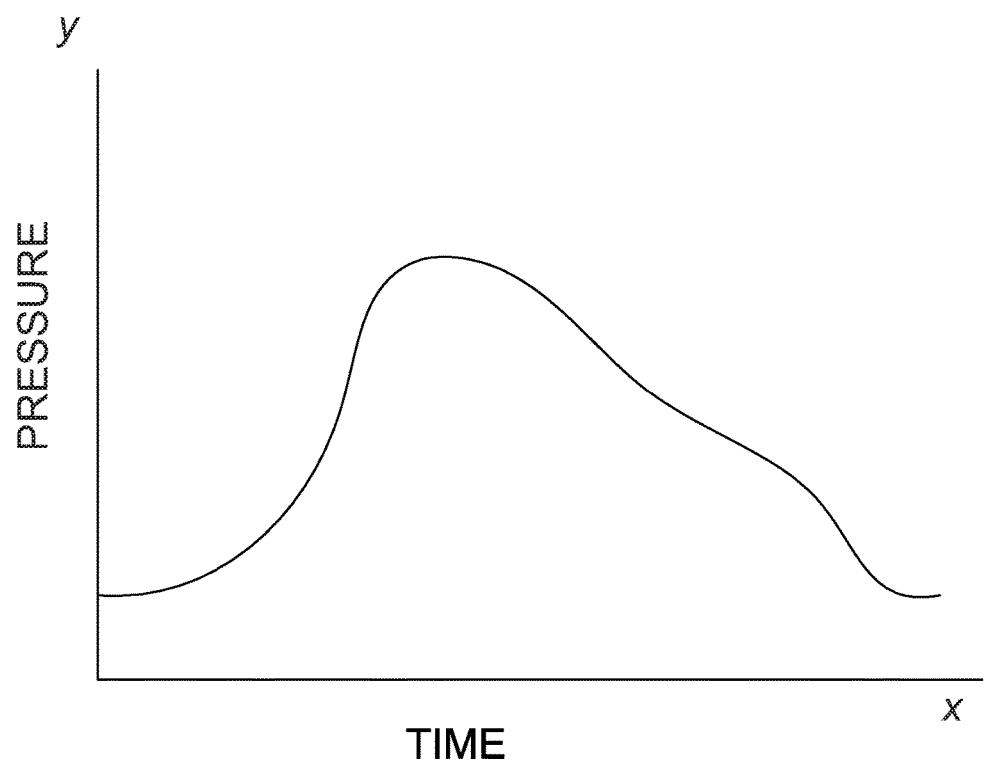
FIG. 6A depicts a schematic diagram of the collection of data for the determination of LVEDP, according to some embodiments of the invention.

FIG. 6A depicts a schematic diagram of the collection of data for the determination of LVEDP, according to some embodiments of the invention.

In some examples of the invention, LVEDP may be calculated by extracting, compiling, and/or using data from 4 or more channels.

A first channel may collect, extract, compile and/or use data derived from a brachial cuff, the cuff, as described for example above. In some embodiments of the invention, an increasing and, in some examples, decreasing pressure value is calculated by sensors associated and/or attached to the brachial cuff, the sensors measuring the applied pressure by the brachial cuff to the brachial artery.

The graph depicts a plot of pressure, as measured by the sensors in the brachial cuff, against time.

Figure 6B:
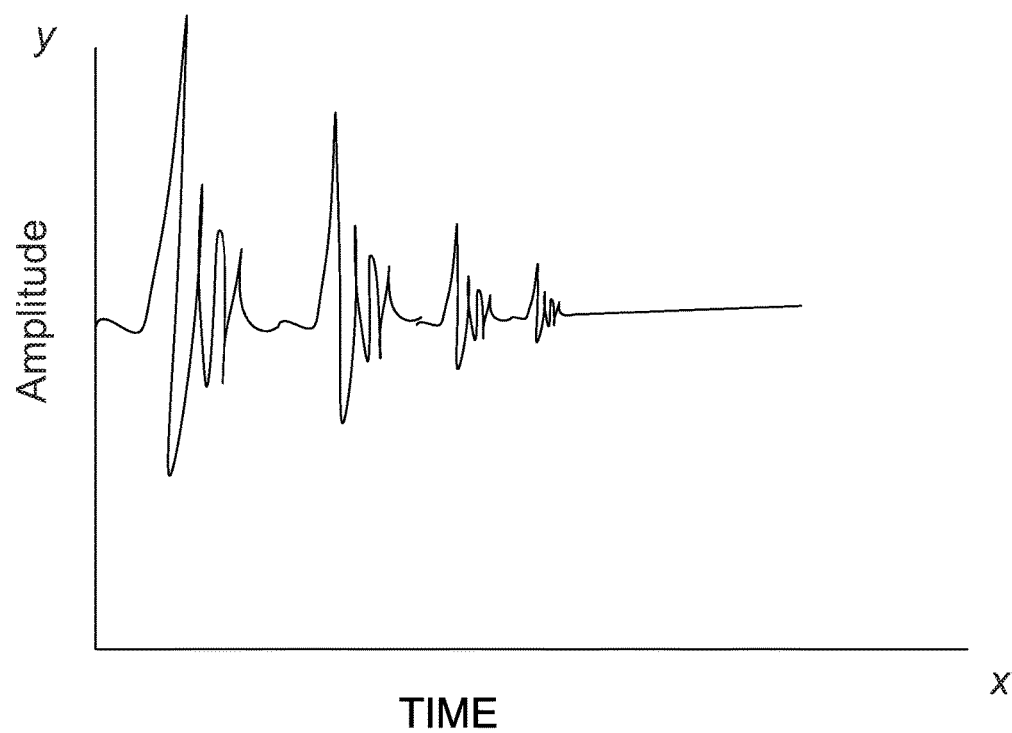
FIG. 6B depicts a schematic diagram of the collection of data for the determination of LVEDP, according to some embodiments of the invention.

FIG. 6B depicts a schematic diagram of the collection of data for the determination of LVEDP, according to some embodiments of the invention.

A second channel may collect, extract, compile and/or use data derived from the brachial cuff, the data relating to the sound of blood flowing past a blockage in the brachial artery, the blockage typically created by the pressure applied by the brachial cuff. E.g., Korotkoff sounds. Korotkoff sounds may be produced in some patients.

FIG. 6B depicts, for example empirically derived audio sounds collected at the site of the brachial cuff, for example, the brachial cuff as described above, after Fourier transformation.

Typically, when a sensor is placed over the brachial artery at the antecubital fossa, no audible sounds can be heard as blood from heart pulses is transmitted smoothly through the arteries via laminar. Similarly, when brachial pressure is applied, e.g., via a brachial cuff, to the brachial artery, wherein the pressure is above the person's systolic blood pressure, there will also be, typically, no audible sounds, as blood flow is occluded in the brachial artery at the cuffs position.

As pressure in the brachial cuff is lowered and the corresponding pressure on the brachial artery is similarly lowered to a value equal to or lower than the systolic blood pressure a first Korotkoff sound may be heard: representing some blood breaking past the stopped blood flow at the site of the brachial cuff. Typically the blood flowing through the brachial artery can be described as flowing in spurts, as pressure in the region continues to drop. These spurts and the resulting turbulence in the arteries produce an audible sound that can be collected, extracted, compiled and/or used by sensors. This sound can be described as a snapping sound.

A clear and tapping-like sound that may be repetitive sounds represents the systolic pressure of the heart.

Figure 6C:
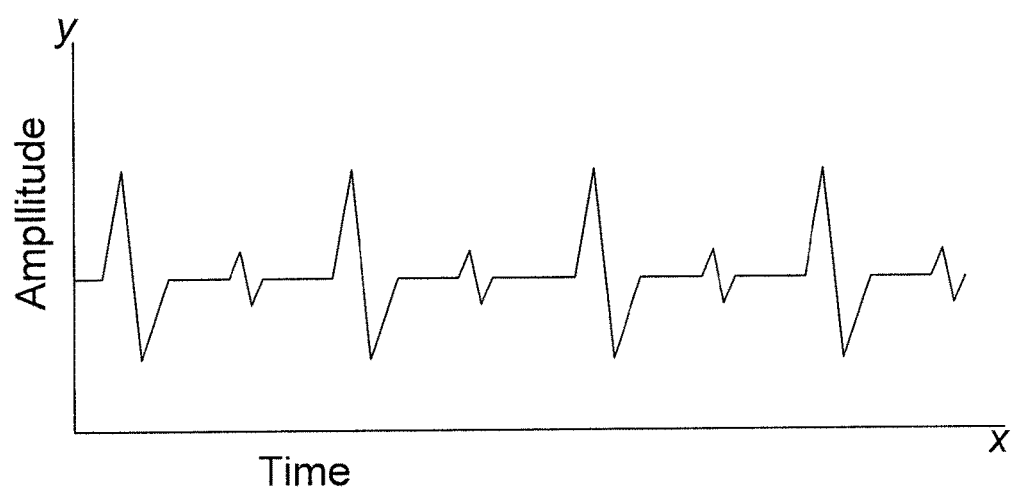
FIG. 6C depicts a schematic diagram of the collection of data for the determination of LVEDP, according to some embodiments of the invention.

FIG. 6C depicts a schematic diagram of the collection of data for the determination of LVEDP, according to some embodiments of the invention.

In some examples of the invention, sensors may further be configured to collect, extract, compile and/or use data derived from the aorta, wherein sounds from the aortic valve opening and closing may be relevant to the determination of LVEDP.

the output, for example, an audio signal, is plotted on the graph as the amplitude of a signal over time.

FIG. 6C depicts, for example, an output for a channel, for example, a channel as described above, wherein the output is empirically derived audio and depicted herein after Fourier transformation, the audio resulting from measurements taken for example at the aorta, the audio synchronized with pressure values as derived from another channel, e.g., a first channel as described above.

Inputs from audio in FIGS. 6B and 6C, may for example be extracted in an analog form and converted to a digital form by a processor, e.g., processor 450 as described above.

In some examples, data from audio sensors and data from pressure sensors, for example, as described above are converted into digital signals using audio to digital transformation hardware. The converted analog signal, e.g., the digital signal is processed by the computer using a Fourier Transform, e.g., a Fast Fourier Transform algorithm such as a time and frequency FFT with a 70% overlap.

In some examples of the invention, a fourth channel may include data from one or a plurality of sensors and/or additional sensors that may be employed at the brachial artery at a point that is not the aorta or the point of the placement of the brachial cuff to collect, extract, compile and/or use data derived from the brachial artery to determine the delay in length along the artery and in time of blood between leaving the aorta and arriving at the brachial cuff. The sensors may also be employed to collect, extract, compile and/or use data related to the propagation speed of the blood through the brachial artery for use in determining LVEDP and other related values.

Figure 7:
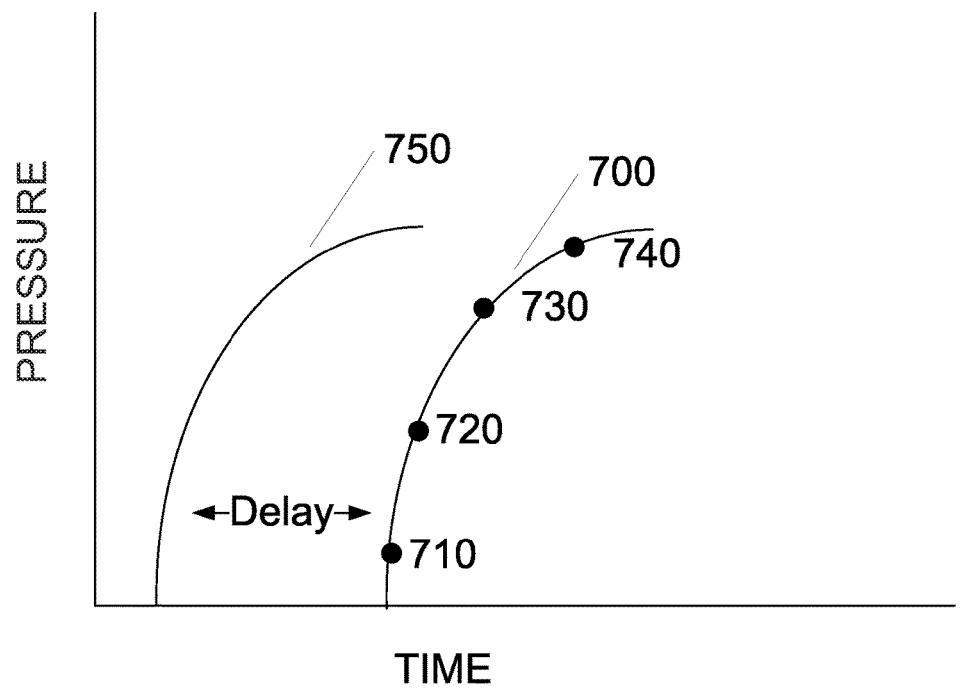
FIG. 7 is a schematic illustration of a method for mathematically deriving LVEDP and other related values, according to some embodiments of the invention.

FIG. 7 is a schematic illustration of a method for mathematically deriving LVEDP and other related values, according to some embodiments of the invention.

A system may be measuring three channels providing three streams of data timelines, for example the channels as described above. A first timeline measures the time as pressure declines in the cuff, heart rhythm and breakthrough at the cuff location.

The system may measure for example, twenty heart strokes. These points plotted can be employed to create a curve represented by a polynomial, for example, a curve 700. The polynomial however represents a delay from the corresponding value representing rising pressure function in the aorta, the pressure function depicted, for example as a curve 750.

A function can be used to describe the pressure within circulation system. A first polynomial may be a fitted function derived from the measured points (e.g., 710, 720, 730, 740) in the form of a target function, e.g., 4th degree polynomial, e.g., $ax^4+bx^3+cx^2+dx+e=y$ where the curve is on a graph depicting time on its x axis and on its y axis, pressure.

And wherein the target function, empirically derived by measurements, is isomorphic to a polynomial representing a time shifted aortic pressure function; i.e., the slope of the empirically derived target polynomial is equal to the slope of the aortic pressure polynomial, where the two polynomials differ by a time shift representing an unknown temporal delay.

Thus: $ax^4+bx^3+cx^2+dx+e=a'z^4+b'z^3+c'z^2+d'z+e'$

Where $z=(x\text{-delay})$

Deriving the equations:

$ax^4+bx^3+cx^2+dx+e=a'z^4+b'z^3+c'z^2+d'z+e'$ $4ax^3+3bx^2+2cx+x=4a'z^3+3b'z^2+2c'z+d'z$ $12ax^2+6bx+2c=-12a'z^2+6zb'+2c'$ $24ax+6b=24a'z+6b'$ $24a=24a'$

Thus: $a=a'$

And $4ax+b=4a'z+b' | a=a'$ $4ax+b=4az+b' | z=x\text{-delay}$ $4ax+b=4a(x\text{-delay})+b'$ Thus: $b+4a(\text{delay})=b'$ And $6ax^2+3bx+c=6az^2+3z(b+4a(\text{delay})+c'|a=a'$ and $b+4a(\text{delay})=b'$ $c=-6a(\text{delay})^2-3b(\text{delay})+c'$ Thus: $c'=c+6a(\text{delay})^2+3b(\text{delay})$ With these equations a new equation can be derived based on empirically derived information wherein the second derivative of the target polynomial is equal to 0 at time 0.

Thus: $12a'x^2+6b'x+c'=0$

Thus: $c'=0$

Given: $c'=c+6a(\text{delay})^2+3b(\text{delay})$

Therefore: $\text{delay} = \dfrac{3b+\left(-\sqrt{9b^2-24ac}\right)}{12a}$

With this mathematical derivation the delay relating to the propagation of blood from the aorta to the occluded position on the brachial artery can be determined.

A new function can be determined that may accurately reflect the pressure curve at the aorta wherein the new polynomial has points corrected from the empirical value to account for a known delay.

LVEDP can be derived from this new function as follows: The new function may be described as an isovolumetric pressure curve wherein the isovolumetric pressure may be described by the function.

$$x = \left(\frac{1}{2} \times p \max\right) \times (1-\cos(\omega t)) + EDP$$

Where: pmax is the pressure that a isovolumetrically contracting left ventricle would produce
ω is the angular frequency;
EDP is an end diastolic pressure value;

The pressure at x, e.g., at the point of time corresponding opening of aortic valve is equal to the diastolic pressure or lowest pressure measured at a break through pointe, e.g. by the brachial cuff, described above.

Therefore:

$$EDP = \left(\frac{1}{2} \times p \max\right) \times (1-\cos(\omega t))$$

At a point x, e.g., at the point of time corresponding opening of aortic valve, the slope if the isovolumetric pressure curve should equal the as described for example above, of the aortic valve since all the force of the contraction is passed to the aorta and represented by max dP/dT.

$$\text{Correspondingly the derivative of} = \left(\frac{1}{2} \times p \max\right) \times (1-\cos(\omega t))$$

equals max dP/dT:

$$\max \frac{dP}{dT} = \left(\frac{1}{2} \times p \max\right) \times \omega \times \sin(\omega \times t)$$

Where ω is the angular frequency
Where $$\omega = \frac{2\pi}{SystolicTime},$$

And t=IVCT.
Systolic time may be approximated by the following equation:

Systolic Time=(IVCT+aortic ejection time)+80 ms

Where (IVCT+aortic ejection time) represents the time interval between 1st sound and 2nd sound
And where 80 ms is the average for Isovolumetric relaxation time.
Therefore:

$$p\max = \frac{(-2 \max dP/dT)}{(\omega \times \sin(\omega \times t))}$$

This now defined pmax can be inserted into $$EDP = \left(\frac{1}{2} \times p \max\right) \times (1-\cos(\omega t))$$

With EDP calculable, max dP/dT is shown to be equal to the dP/dT of the ventricle at the opening of the aortic valve. These values allow for the calculation of LVEDP, as described, for examples above.

The values of the target function, may in some embodiments of the invention be derived from iterative experimental derivations, for example calculating values of the channels, as discussed, for example, above (excepting, for example the fourth channel, as described above) over the course of twenty seconds, or for example, 15 to 30 measurements over a short time period. The values for the channel may be based on measured data from a device that measures blood pressure as a function of time when a cuff provides external pressure to the brachial artery. The blood pressure exerted on the artery measured when there is a breakthrough at the location of the brachial cuff. The time is calculated from the first sound of the heart stroke.

Figure 8:
FIG. 8 depicts a schematic illustration of a device for determining ischemic conditions in a patient, according to embodiments of the invention.
Figure 8:
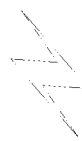

FIG. 8 depicts a schematic illustration of a device for determining ischemic conditions in a patient, according to embodiments of the invention.

Ischemic heart disease is one of the most common causes of death in many Western and developed countries. In some instances ischemia can occur when heart muscle (myocardium) receives too little oxygenated blood flow. When there is an over-accumulation of cholesterol-rich plaques in the coronary arteries, ischemia can result.

Ischemia can be indicated by rapid changes in max dP/dT, where max dP/dT is the maximum isovolumetric pressure rate in the left ventricle, as described above. In some embodiments of the invention, a device that measures real-time changes in max dP/dT, can be used, in some examples, to predict asymptomatic early ischemia or otherwise heretofore not detected ischemia.

In some embodiments of the invention, a ischemia determining device 810 may measure max dP/dT, as described above and as its derivation, for example, as described above. The device may have multiple sensors 820. The sensors may be implanted or external and may be connected wirelessly or via a wired or other connection to ischemia determining device 810. Ischemia determining device 810 may further be able to provide an output 830, wherein output 830 may include a display, a audio device, or a device configured to interact telephonically, via the internet or via other transmissions methodologies with other devices located nearby or located at a distance.

In some embodiments of the invention, the output may be provided to a health practitioner, a health clinic, a hospital, a reporting station, a physician, and/or any particular device, the output configured such that it might provide a signal, warning and/or other communication of an ischemic event in the person being monitored by ischemia determining device 810.

Examples of the present invention may include apparatuses for performing the operations described herein. Such apparatuses may be specially constructed for the desired purposes, or may comprise computers or processors selectively activated or reconfigured by a computer program stored in the computers. Such computer programs may be stored in a computer-readable or processor-readable non-transitory storage medium, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions. It will be appreciated that a variety of programming languages may be used to implement the teachings of the invention, as described herein. Examples of the invention may include an article such as a non-transitory computer or processor readable non-transitory storage medium, such as for example, a memory, a disk drive, or a USB flash memory encoding, including or storing instructions, e.g., computer-executable instructions, which when executed by a processor or controller, cause the processor or controller to carry out methods disclosed herein. The instructions may cause the processor or controller to execute processes that carry out methods disclosed herein.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A device for determining a cardiac function parameter, the device comprising:
   a sonic sensor configured to determine a closure of a mitral valve and an aortic valve;
   a pressure cuff configured to apply occluding pressure to an artery;
   a sensing unit coupled to the pressure cuff; and
   a processing unit configured to:
   (i) determine, for each cardiac cycle, a blood breakthrough pressure value and a corresponding time value from a closing of the mitral valve, wherein the determining is based on sensor measurements from the sonic sensor and the sensing unit, and wherein each cardiac cycle is one from a plurality of cardiac cycles during deflation of the pressure cuff,
   (ii) curve-fit, for at least some of the plurality of cardiac cycles, at least some of the blood breakthrough pressure values and the corresponding time values, and
   (iii) determine a value of at least one cardiac function parameter based on a maximum pressure rate in a left ventricle after an opening of the aortic valve computed using at least one derivative of the curve-fit,
   wherein the at least one cardiac function parameter comprises left ventricle end diastolic pressure (LVEDP).

2. The device of claim 1, wherein the at least one cardiac function parameter further comprises at least one of: isovolumetric contraction time, systemic vascular resistance, and central aortic pressure.

3. The device of claim 1, wherein the sonic sensor is a microphone.

4. The device of claim 1, wherein the sensing unit comprises a pressure sensor.

5. The device of claim 1, wherein the sensing unit comprises a Doppler sensor.

6. The device of claim 1, wherein the processing unit is further configured to iteratively calculate cardiac pressure and related values by calculating a slope of a tangent to a pressure waveform at a time point where the aortic valve opens.

7. The device of claim 1, wherein the curve-fit is with a polynomial function, wherein the processing unit is configured to calculate an integral of a second derivative of the polynomial function.

8. The device of claim 1, wherein the processing unit is further configured to calculate the LVEDP using the equation:

$$EDP = pov - \left(\frac{1}{2} \times \frac{\max \frac{dP}{dT}}{\omega}\right) \times (1 - \cos(\omega t))$$

where:
max dP/dT is a maximum isovolumetric pressure rate in the left ventricle; ω is an angular frequency; EDP is an end diastolic pressure value; pov is a pressure at opening of the aortic valve; and t is the time to opening of the aortic valve.

9. The device of claim 1, wherein the at least one cardiac function parameter further comprises systemic vascular resistance, and wherein the processing unit is configured to determine the systemic vascular resistance by comparing a portion of a theoretical isovolumetric pressure function with an empirical central aortic pressure function.

10. The device of claim 1, configured to export data to a monitoring unit.

11. A device for determining a cardiac function parameter, the device comprising:
a sonic sensor configured to determine a closure of a mitral valve and an aortic valve;
a pressure sensor configured to be positioned within a central aorta of a patient; and
a processing unit configured to:
(i) determine, for each cardiac cycle, a blood breakthrough pressure value and a corresponding time value from a closing of the mitral valve, wherein the determining is based on sensor measurements from the sonic sensor and the sensing unit, and wherein each cardiac cycle is one from a plurality of cardiac cycles during deflation of the pressure cuff,
(ii) curve-fit, for at least some of the plurality of cardiac cycles, at least some of the blood breakthrough pressure values and the corresponding time values, and
(iii) determining a value of at least one cardiac function parameter based on a maximum pressure rate in a left ventricle after an opening of the aortic valve computed using at least one derivative of the curve-fit,
wherein the at least one cardiac function parameter comprises left ventricle end diastolic pressure (LVEDP).

12. The device of claim 11, wherein the sonic sensor is a microphone.

13. The device of claim 11, wherein the processing unit is further configured to export data to a monitoring unit.

14. The device of claim 11, wherein the at least one cardiac function parameter further comprises at least one of: isovolumetric contraction time, systemic vascular resistance, and central aortic pressure.

15. The device of claim 11, wherein the at least one cardiac function parameter further comprises systemic vascular resistance, and wherein the processing unit is configured to determine the systemic vascular resistance by comparing a portion of a theoretical isovolumetric pressure function with an empirical central aortic pressure function.

16. A method for determining a cardiac function parameter, the method comprising using a processing unit to:
collect timing data of a closure of a mitral valve and an aortic valve using a sonic sensor;
using a sensing unit coupled to a pressure cuff, determine for each cardiac cycle, a blood breakthrough pressure value and corresponding time value from a closing of the mitral valve, wherein the determining is based on sensor measurements from the sonic sensor and the sensing unit, and wherein each cardiac cycle is one from a plurality of cardiac cycles during deflation of the pressure cuff;
curve-fit, for at least some of the plurality of cardiac cycles, at least some of the blood breakthrough pressure values and the corresponding time values; and
determine a value of at least one cardiac function parameter based on a maximum pressure rate in a left ventricle after an opening of the aortic valve computed using at least one derivative of the curve-fit,
wherein the at least one cardiac function parameter comprises left ventricle end diastolic pressure (LVEDP).

17. The method of claim 16, wherein said at least one cardiac function parameter further comprises at least one of: isovolumetric contraction time, systemic vascular resistance, and central aortic pressure.

18. The method of claim 16, further comprising using the processing unit to iteratively calculate cardiac pressure and related values by calculating a slope of a tangent to a pressure waveform at a time point where the aortic valve opens.

19. The method of claim 16, further comprising using the processing unit to calculate the LVEDP using the equation:

$$EDP = pov - \left(\frac{1}{2} \times \frac{\max \frac{dP}{dT}}{\omega}\right) \times (1 - \cos(\omega t))$$

where:
max dP/dT is a maximum isovolumetric pressure rate in the left ventricle; ω is an angular frequency; EDP is an end diastolic pressure value; pov is a pressure at opening of the aortic valve; and t is a time to opening of the aortic valve.

20. The method of claim 16, wherein the at least one cardiac function parameter further comprises systemic vascular resistance, and wherein the method further comprises using the processing unit to determine the systemic vascular resistance by comparing a portion of a theoretical isovolumetric pressure function with an empirical central aortic pressure function.

* * * * *